(12) United States Patent
Lyons et al.

(10) Patent No.: US 10,927,341 B2
(45) Date of Patent: Feb. 23, 2021

(54) MULTI-FUNCTIONAL FLUID FLOW DEVICE

(71) Applicant: University of Maryland, Baltimore, Baltimore, MD (US)

(72) Inventors: James Lyons, York, PA (US); Christopher Ward, Baltimore, MD (US); Joseph Stains, Laurel, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 150 days.

(21) Appl. No.: 15/466,255

(22) Filed: Mar. 22, 2017

(65) Prior Publication Data

US 2017/0276666 A1   Sep. 28, 2017

Related U.S. Application Data

(60) Provisional application No. 62/311,654, filed on Mar. 22, 2016.

(51) Int. Cl.
| | |
|---|---|
| *B01L 3/00* | (2006.01) |
| *C12N 5/00* | (2006.01) |
| *G01N 33/543* | (2006.01) |
| *C12M 1/32* | (2006.01) |
| *C12M 1/42* | (2006.01) |

(52) U.S. Cl.
CPC ............ *C12N 5/00* (2013.01); *B01L 3/50853* (2013.01); *C12M 23/12* (2013.01); *C12M 35/04* (2013.01); *G01N 33/54366* (2013.01); *B01L 2200/026* (2013.01); *B01L 2300/046* (2013.01); *B01L 2300/0829* (2013.01)

(58) Field of Classification Search
CPC ........................ B01L 3/502; B01L 2200/026
USPC ................... 422/558, 549, 546, 562
See application file for complete search history.

(56) References Cited

U.S. PATENT DOCUMENTS

| | | | |
|---|---|---|---|
| 5,928,945 A | 7/1999 | Seliktar et al. | |
| 6,472,202 B1 | 10/2002 | Banes | |
| 6,586,235 B1 | 7/2003 | Banes | |
| 9,006,149 B2 | 4/2015 | Garcia-Cardena et al. | |
| 2005/0003944 A1* | 1/2005 | Rivalier | B01D 11/048 494/22 |
| 2006/0234372 A1 | 10/2006 | Donahue | |
| 2008/0057571 A1 | 3/2008 | Loboa et al. | |
| 2015/0023911 A1 | 1/2015 | Schililng et al. | |

OTHER PUBLICATIONS

Jaalouk, D.E. et al., "Mechanotransduction gone awry", 2009. Nat. Rev. Mol. Cell Biol. 10, 63-73.

(Continued)

*Primary Examiner* — Natalia Levkovich
(74) *Attorney, Agent, or Firm* — Riverside Law LLP

(57) ABSTRACT

The present invention relates to a fluid flow device. The device includes an elongate body having a proximal end, a distal end, and a length therebetween, at least one source fluid inflow port, at least one waste fluid outflow port, at least one well inlet port positioned at the distal end of the elongate body, at least one well outlet port positioned at the distal end of the elongate body, at least one conduit connecting the at least one source fluid inflow port to the at least one well inlet port, and at least one conduit connecting the at least one waste fluid outflow port to the at least one well outlet port.

16 Claims, 15 Drawing Sheets

(56) References Cited

OTHER PUBLICATIONS

Bonewald, L.F. et al., "Osteocytes, Mechanosensing and Wnt Signaling", 2008. Bone 42, 606-615.

Klein-Nulend, J. et al., "Mechanosensation and transduction in osteocytes", 2013. Bone 54, 182-190.

Oftadeh, R. et al., "Biomechanics and Mechanobiology of Trabecular Bone: A Review", 2015. J. Biomech. Eng. 137.

Rubin, J. et al., "Molecular pathways mediating mechanical signaling in bone", 2006. Gene 367,1-16.

Thompson, W.R., et al., "Mechanical Regulation of Signaling Pathways in Bone", 2012. Gene 503,179-193.

Turner, C.H. et al., "Mechanobiology of the Skeleton", 2009. Sci. Signal. 2(68):pt3.

De Castro, L.F. et al., "VEGF Receptor 2 (VEGFR2) Activation Is Essential for Osteocyte Survival Induced by Mechanotransduction", 2015. J. Cell. Physiol. 230, 278-285.

Espinha, L.C. et al., "Oscillatory Fluid Flow Influences Primary Cilia and Microtubule Mechanics", 2014. Cytoskeleton 71,435-445.

Genetos, D.C. et al., "Fluid Shear-Induced ATP Secretion Mediates Prostaglandin Release in MC3T3-E1 Osteoblasts", 2005. J. Bone Mineral. Res.: Off. J. Am. Soc. Bone Mineral. Res. 20,41-49.

Michael Delaine-Smith, R. et al., "Preclinical models for in vitro mechanical loading of bone-derived cells", 2015. BoneKEy Rep. 4, 728.

Aryaei, A. et al., "The effect of oscillatory mechanical stimulation on osteoblast attachment and proliferation", 2015. Mater. Sci. Eng. C, Mater. Biol. Appl. 52, 129-134.

Burra, S. et al., "Dendritic processes of osteocytes are mechanotransducers that induce the opening of hemichannels", 2010. Proc. Natl. Acad. Sci. U.S.A.107, 13648-13653.

Shemesh, J. et al., "Flow-induced stress on adherent cells in microfluidic devices", 2015. Lab. Chip 15, 4114-4127.

Polacheck, W.J. et al., "Microfluidic platforms for mechanobiology", 2013. Lab on a Chip 13, 2252-2267.

Ostrowski, M.A. et al., "Multiplexed Fluid Lfow Device to Study Cellular Response to Tunable Shear Stress Gradients", A.R. Annals of Biomed Engr. Jul. 2016. 44(7), 2261-2272.

Balaguru, U.M. et al., "Distrubed flow mediated modulation of shear forces on endothelial plane: A proposed model for studying endothelium around atherosclerotic plaques", 2016 Scientific Reports, 6, 27304.

Lyons, J.S. et al., "Novel multi-functional fluid flow decive for studying cellular mechanotransduction", 2016, J Biomechanics, 49, 4173-4179.

Bashir, R. "Introduction to Bio-Chip, Biosensors, BioMEMS", Laboratory of Integrated Biomedical Micro/Nanotechnology and Applications (LIBNA), School of Electrical and Computer Engineering, Department of biomedical Engineering, Purdue University, West Lafayette, Indiana. <http://libna.mntl.illinois.edu/pdf/Lecture_1_biochips.pdf>.

* cited by examiner

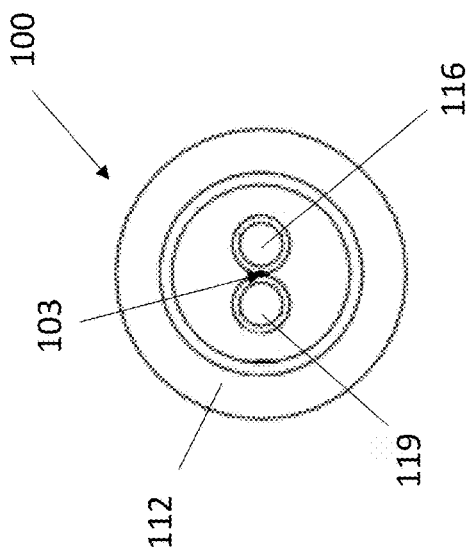
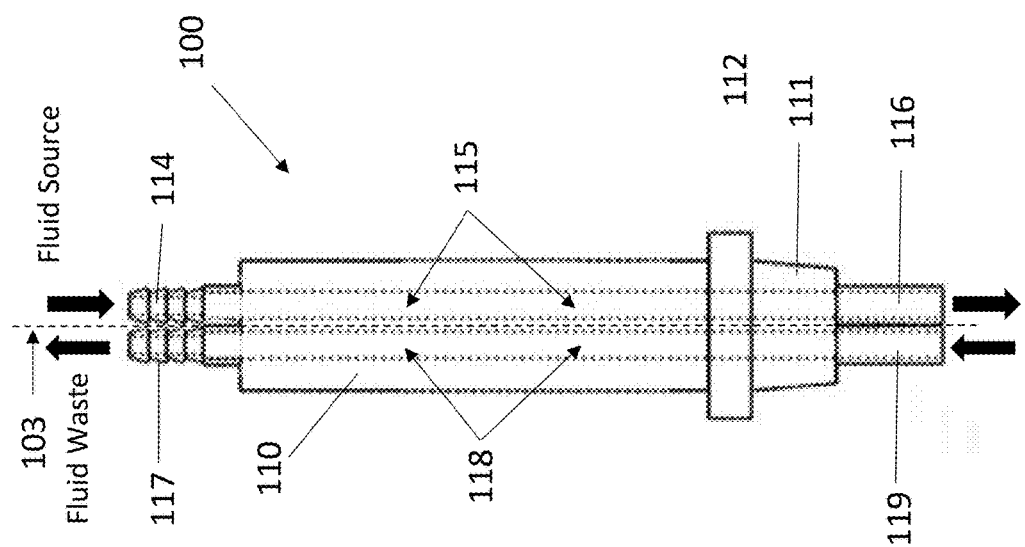
Figure 4B
Figure 4A

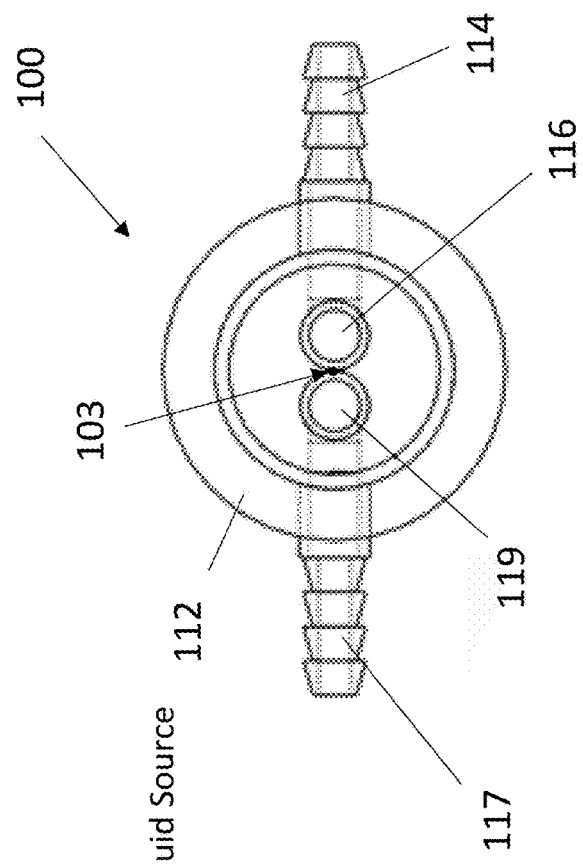
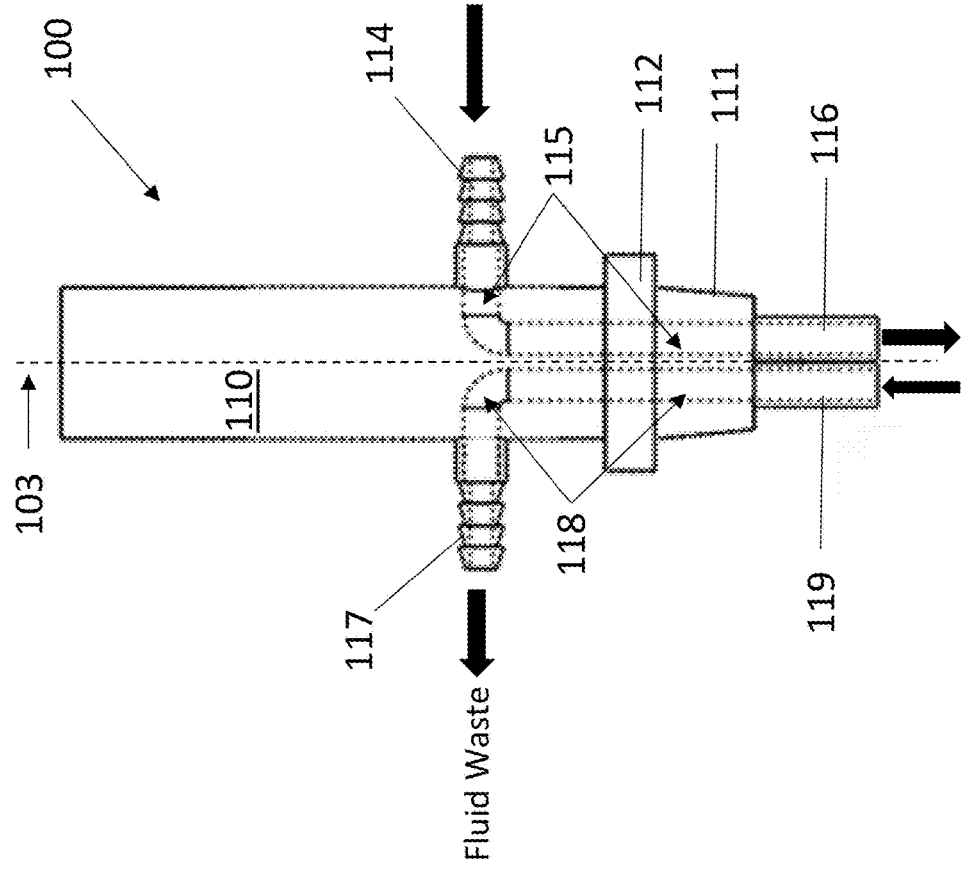
Figure 5B
Figure 5A

MULTI-FUNCTIONAL FLUID FLOW DEVICE

CROSS-REFERENCE TO RELATED APPLICATIONS

This application claims the benefit of priority under 35 U.S.C. § 119(e) to U.S. Provisional Patent Application No. 62/311,654, filed Mar. 22, 2016, the contents of which are incorporated by reference herein in their entirety.

STATEMENT REGARDING FEDERALLY SPONSORED RESEARCH OR DEVELOPMENT

This invention was made with government support under grant number AR063631 awarded by the National Institutes of Health (NIH). The government has certain rights in the invention.

BACKGROUND OF THE INVENTION

Cells respond to their mechanical environment by activating biochemical signaling pathways, a process known as mechanotransduction. Mechanotransduction regulates diverse physiologic function in healthy cells, and burgeoning evidence implicates dysregulation of mechanotransduction cascades in disease pathology (Jaalouk, D. E., Lammerding, J., 2009. Nat. Rev. Mol. Cell Biol. 10, 63-73.). Given that these mechanotransduction pathways often integrate multiple signaling events, there is a growing interest to identify key signaling nodes that can be targeted to modulate outputs that drive physiology or disease.

In the skeletal system, osteocytes sense mechanical strain within bone and respond with mechanotransduction signals (e.g., calcium ($Ca2^+$), nitric oxide, extracellular ATP) and the expression of factors (e.g., receptor activator of NFκB ligand (RANKL) and sclerostin) that control the activity of bone resorbing osteoclasts and bone forming osteoblasts (Bonewald, L. F., Johnson, M. L., 2008. Bone 42, 606-615; Klein-Nulend, J., Bakker, A. D., Bacabac, R. G., Vatsa, A., Weinbaum, S., 2013. Bone 54, 182-190; Oftadeh, R., Perez-Viloria, M., Villa-Camacho, J. C., Vaziri, A., Nazarian, A., 2015. J. Biomech. Eng. 137; Rubin, J., Rubin, C., Jacobs, C. R., 2006. Gene 367, 1-16; Thompson, W. R., Rubin, C. T., Rubin, J., 2012. Gene 503, 179-193; Turner, C. H., Warden, S. J., Bellido, T., Plotkin, L. I., Kumar, N., Jasiuk, I., Danzig, J., Robling, A. G., 2009. Sci. Signal. 2). Given that fluid flow through the lacunar-canalicular network generates shear stress driving mechanotransduction in bone (Klein-Nulendetal, 2013), fluid flow is most often used to interrogate osteocyte response to mechanical load.

A number of commercially available systems have been developed to model fluid flow in osteoblast and osteocyte-like cultured cells and each has its own limitations, such as limited throughput and/or functionality (de Castro, L. F., Maycas, M., Bravo, B., Esbrit, P., Gortazar, A., 2015. J. Cell. Physiol. 230, 278-285; Espinha, L. C., Hoey, D. A., Fernandes, P. R., Rodrigues, H. C., Jacobs, C. R., 2014. Cytoskeleton 71, 435-445; Genetos, D. C., Geist, D. J., Liu, D., Donahue, H. J., Duncan, R. L., 2005. J. Bone Mineral. Res.: Off. J. Am. Soc. Bone Mineral. Res. 20, 41-49; Michael Delaine-Smith, R., Javaheri, B., Helen Edwards, J., Vazquez, M., Rumney, R. M., 2015. BoneKEy Rep. 4, 728.) and do-it-yourself (Aryaei, A., Jayasuriya, A. C., 2015. Mater. Sci. Eng. C, Mater. Biol. Appl. 52, 129-134; Burra, S., Nicolella, D. P., Francis, W. L., Freitas, C. J., Mueschke, N. J., Poole, K., Jiang, J. X., 2010. Proc. Natl. Acad. Sci. U.S.A. 107, 13648-13653; Shemesh, J., Jalilian, I., Shi, A., HengYeoh, G., KnotheTate, M. L., Ebrahimi Warkiani, M., 2015. Lab. Chip 15, 4114-4127). Several of these systems have been developed to deliver physiologic fluid flow shear stress to osteoblast and osteocyte-like cells in culture. These systems range from simple experimental conditions where a droplet of buffer is released from a pipette at a set height, to complex fluid flow systems such as the FlexCell Streamer.

While all the current models can deliver physiologically relevant fluid flow to cells in culture and generate physiologically relevant fluid shear stresses, each of these systems has their own disadvantages. Several of these systems require plating on proprietary slides, dishes or containers restricting the flexibility that the investigator has over plating surface conditions or geometries. Additionally, there is a large financial burden when purchasing these existing multi-component systems rather than being able to integrate a fluid flow device into commonly used cell culture systems and flow apparatus. Furthermore, many of the currently available flow systems are designed to only to test one sample of cells at a time in a low-throughput manner rather than being able to concurrently test multiple dishes or wells of cultured cells.

Thus, there is a need in the art for improved devices for culturing cells under physiological flow conditions offering high-throughput options with a cost-effective design. The present invention satisfies this unmet need.

SUMMARY OF THE INVENTION

A fluid flow device is described. The device includes an elongate body having a proximal end, a distal end, and a length therebetween, at least one source fluid inflow port, at least one waste fluid outflow port, at least one well inlet port positioned at the distal end of the elongate body, at least one well outlet port positioned at the distal end of the elongate body, at least one conduit connecting the at least one source fluid inflow port to the at least one well inlet port, and at least one conduit connecting the at least one waste fluid outflow port to the at least one well outlet port.

In one embodiment, one of the at least one well inlet ports is positioned in line with a central axis of the elongate body. In another embodiment, the at least one well inlet port extends from the distal end of the elongate body further than the at least one well outlet port. In another embodiment, the at least one well inlet port and the at least one well outlet port extend the same distance from the distal end of the elongate body. In another embodiment, the at least one conduit connecting the at least one source fluid inflow port to the at least one well inlet port, and the at least one conduit connecting the at least one waste fluid outflow port to the at least one well outlet port are positioned within the elongated body. In another embodiment, the distal end of the elongate body is tapered. In another embodiment, the at least one source fluid inflow port and the at least one waste fluid outflow port each extend outwardly from the length of the elongate body. In another embodiment, the at least one source fluid inflow port and the at least one waste fluid outflow port each extend upward from the proximal end of the elongate body. In another embodiment, the device further comprises a flange positioned at a distal region of the elongate body, wherein the flange is capable of sealing the distal end of the elongate body within a culturing well Also described is a high-throughput fluid flow assembly. The assembly includes a plurality of fluid flow devices, wherein the fluid flow devices are physically connected such that a central axis of each elongate body of the fluid flow devices are parallel. In one embodiment, the source fluid inflow ports of each respective fluid flow device is fluidly connected to shared fluid source. In another embodiment, the waste fluid outflow ports or each respective fluid flow device is fluidly connected to shared fluid reservoir.

Also described is a fluid flow kit. The kit includes at least one fluid flow device and an instruction material.

Also described is a method of applying fluid flow to biological cells in a culturing well. The method includes the steps of positioning a fluid flow device in a culturing well of a cell culture plate, such that the at least one well inlet port and at least one outlet port are positioned within the well, and flowing a fluid through the device of claim 1, wherein the fluid applies a shear stress to the cells in the culturing well. In one embodiment, the step of flowing fluid through the fluid flow device further comprises a pump in line with the at least one source fluid inflow port. In another embodiment, the flow rate of the fluid is adjustable. In another embodiment, the shear stress is about 4 dynes/cm$^2$.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

FIGS. 4A and 4B are front and bottom views of an alternative embodiment of an exemplary FFD of the present invention.

FIGS. 5A and 5B are front and bottom views of another alternative embodiment of an exemplary FFD of the present invention.

FIG. 6A depicts an example of the multichannel peristaltic pump used when multiplexing the FFD and a computer rendering of the FFD multiplexed in a single 96-well assay plate across 6 independent wells. FIG. 6B depicts western blot analysis of UMR106 cells simultaneously exposed to fluid flow in separate wells. Image J quantification of western blot analysis relative to GAPDH. Asterisks indicate statistical significance at p<0.05. Double asterisks (**) indicate statistical significance at p<0.01.

FIG. 7A illustrates simulated dynamic pressure within the FFD and well. FIG. 7B depicts simulated velocity within the FFD and well. FIG. 7C depicts simulated turbulence intensity within the FFD and well.

FIGS. 9A and 9B illustrate trajectories of flow from the front section view and a top view. FIG. 9C illustrates an up-close view of the inlet and outlet trajectories within the well of the plate. Data were determined using SolidWorks 2015 Flow Simulation software.

FIG. 10 depicts Fluo-4Ca$^{2+}$ indicator dye fluorescence before (basal) and during flow (response) of cells seeded in both the Ibidi chambers and a 96-well plate with the FFD. Red line in image sequence indicates start and duration of fluid flow. Highlighted boxes indicate peak calcium responses. FIG. 11 depicts traces of average Ca$^{2+}$ indicator dye fluorescence intensity over time scaled to same basal level of fluorescence intensity are shown in bold lines. Gray overlay traces represent the Ca$^{2+}$ response of individual cells in the well. FIG. 12 depicts peak change in Ca$^{2+}$ indicator dye fluorescence intensity and elevation/decay kinetics of Ca$^{2+}$-dependent fluorescence. NS, not statistically significant.

DETAILED DESCRIPTION

Definitions

Figure 1:
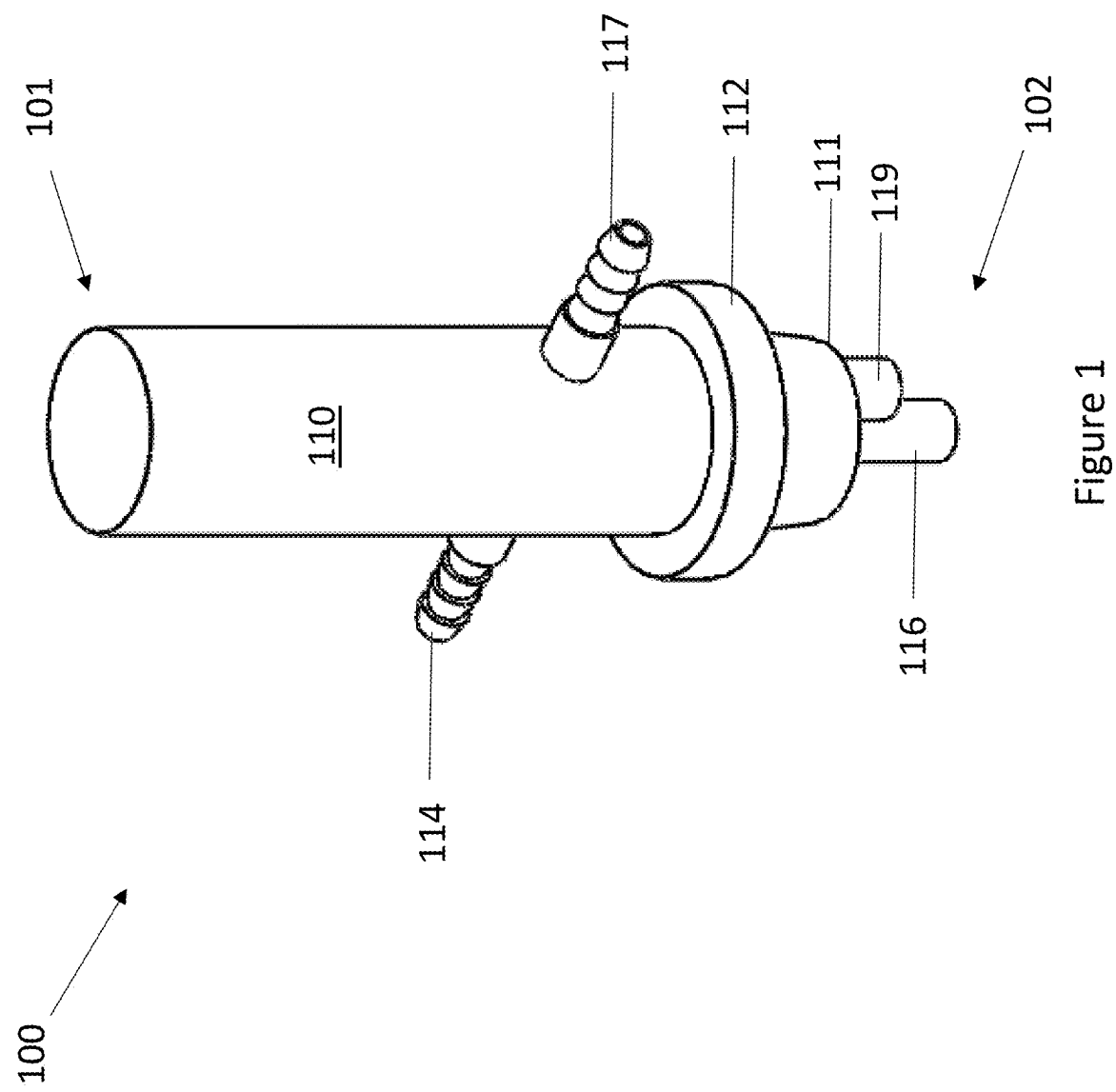
FIG. 1 is an isometric view of an exemplary fluid flow device (FFD) of the present invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to a fluid flow device comprising inlet and outlet ports, inflow ports and outflow ports, used for applying shear stress to cultured cells. The invention provides a unique platform for applying physiological shear stress and pressure to cultured cells that mimics the shear stress of the in vivo microenvironment. The versatility in its function provides the fluid flow device with a significant advantage over currently available models. The present invention can be used to image live cells in real-time during fluid flow by placing the device in an optics plate, such as an optically clear culture plate, or the like. Also, the present invention can form a fluid flow device assembly used for high-throughput molecular and biochemical analysis of cells following fluid flow. This is important when considering potential variability between devices when performing a variety of experiments with differing output measures. By using the same device for every experiment rather than a device specifically for imaging and another device specifically for molecular and biochemical analyses, the possibility of obtaining variable results due to the differences in flow properties from one device to the next is significantly reduced. Importantly, the device of the present invention provides a distinct improvement over current models by providing the ability to multiplex the device. One can use multiple devices in the same plate with a multichannel pump to obtain fully independent replicates for each sample. Similarly, multiplexing allows for comparing multiple samples that are subjected to identical flow under similar conditions at the same time. Lastly, a significant advantage of the present invention is the cost savings, in that the device and assembly described herein offers a low-cost alternative to existing models.

Fluid Flow Device

Referring now to FIG. 1, an exemplary fluid flow device (FFD) 100 of the present invention is shown. FFD 100 generally comprises an elongate body 110 having a proximal end 101 and a distal end 102, a support flange 112, a source fluid inflow port 114, a waste fluid outflow port 117, a well inlet port 116, and a well outlet port 119.

Figure 2A:
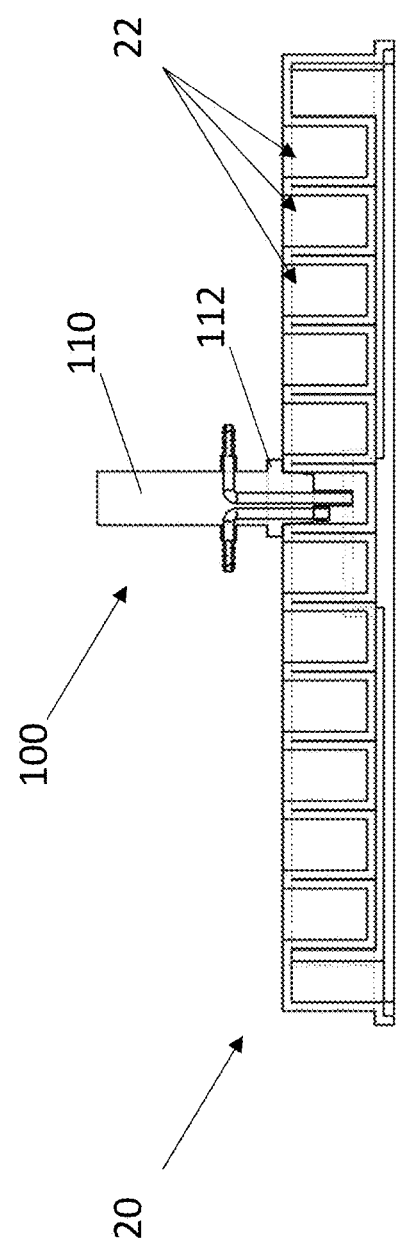
FIGS. 2A and 2B are front and isometric views of a cell culturing plate with the FFD of FIG. 1 positioned within a well.
Figure 2B:
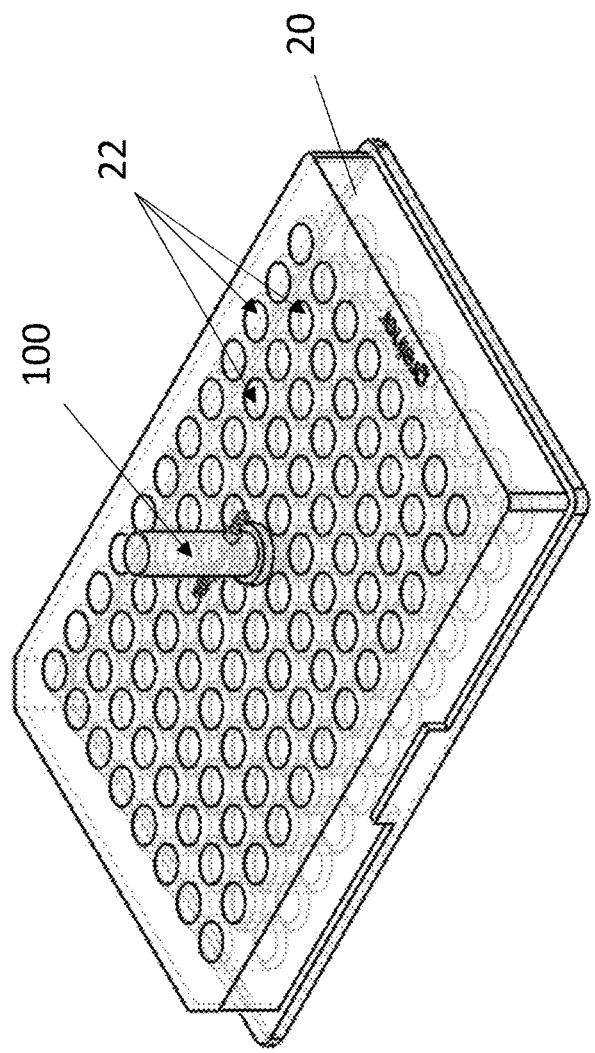

Referring also to FIGS. 2A and 2B, elongate body 110 has a distal region 111 that is sized to fit into a desired well 22 of a culturing plate 20, with the support flange 112 resting on top of the well plate surface to ensure well inlet and outlet ports 116 and 119 are positioned fully within well 22 at the desired depth. In some embodiments, support flange 112 may form a seal with the top opening of well 22. In some embodiments, distal region 111 may be tapered to provide a friction fit, or otherwise engage the opening of well 22 snuggly. In other embodiments, the proximal region of elongate body 110 may be connected to an automated or robotic system for placing and removing one or more FFDs 100 into and out of the targeted wells 22 of culturing plate 20.

Figure 6A:
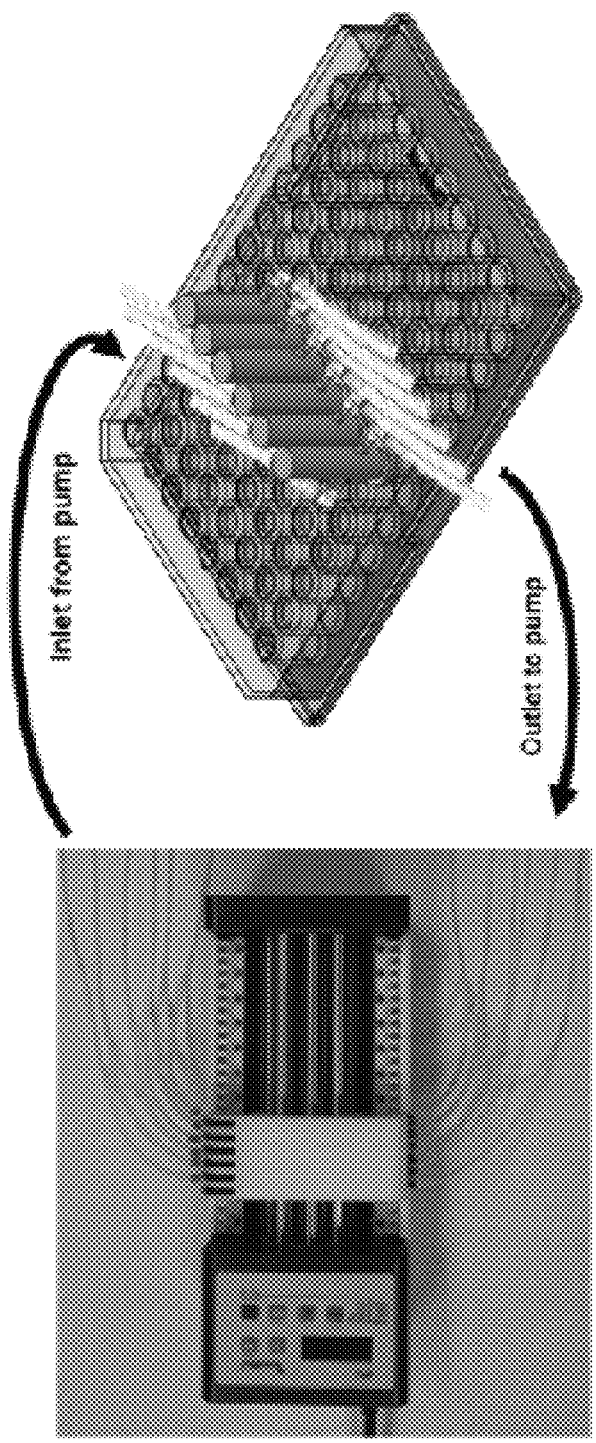
FIG. 6A and FIG. 6B depict the results of experiments demonstrating the multiplexing capability of the FFD.
Figure 6B:
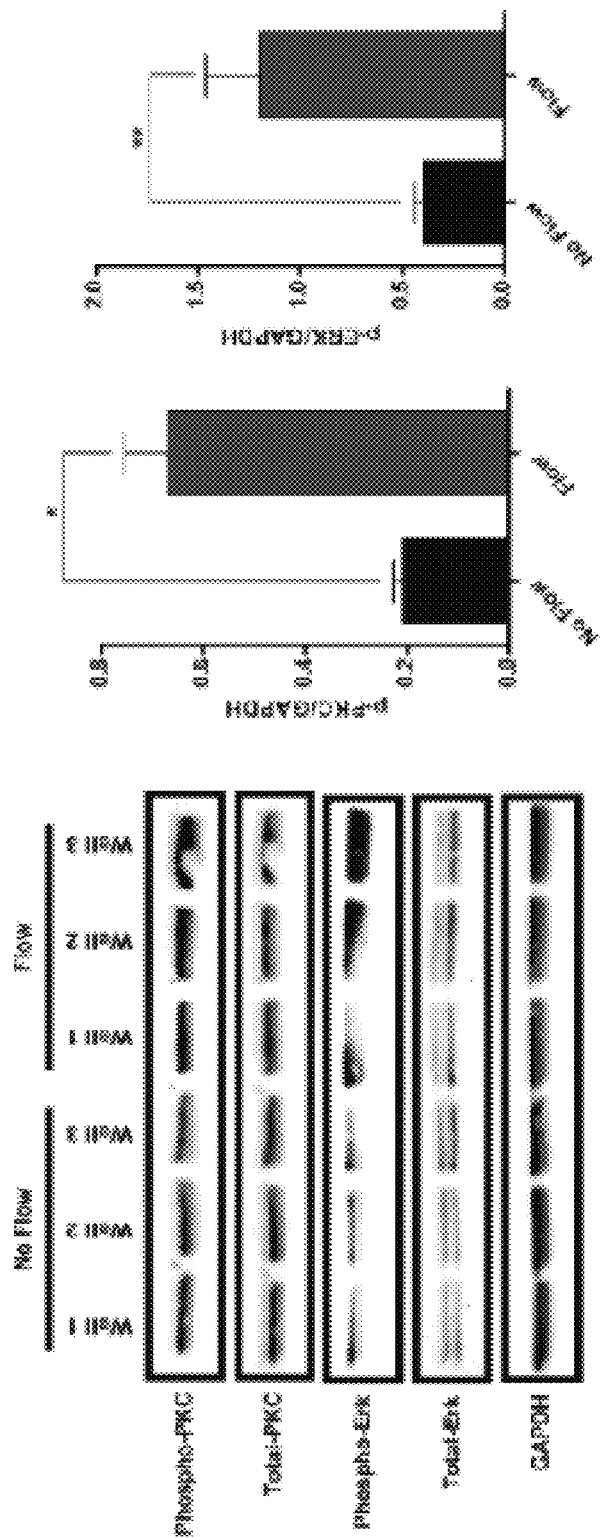

Distal region 111 of elongate body 110 may be any shape, provided it fits, loosely or snuggly, within the opening of the desired well 22. The portion of elongate body 110 proximal to support flange 112 may be any desired shape, such as cylindrical or rectangular, for example. In certain embodiments, elongate body 110 proximal to support flange 112 is sized and shaped so that multiple FFDs 100 can be efficiently stacked, such that each FFD 100 can be positioned in all or any number of adjacent wells 22 within a multi-well culturing plate 20, for example as shown in FIG. 6. Support flange 112 may likewise be any shape, provided that it suitably extends beyond at least a portion of the perimeter of the desired well opening. In some embodiments, the overall length of FFD 100 may be between 20 mm and 100 mm. In some embodiments, the overall outer diameter or width of FFD 100 may be between 10 mm and 200 mm. However, it should be appreciated that the overall size of FFD 100 is not limited, and will be generally dictated according to the size of the culturing well or multi-well plate for which the FFD is designed for use with.

Figures 3A, 3B:
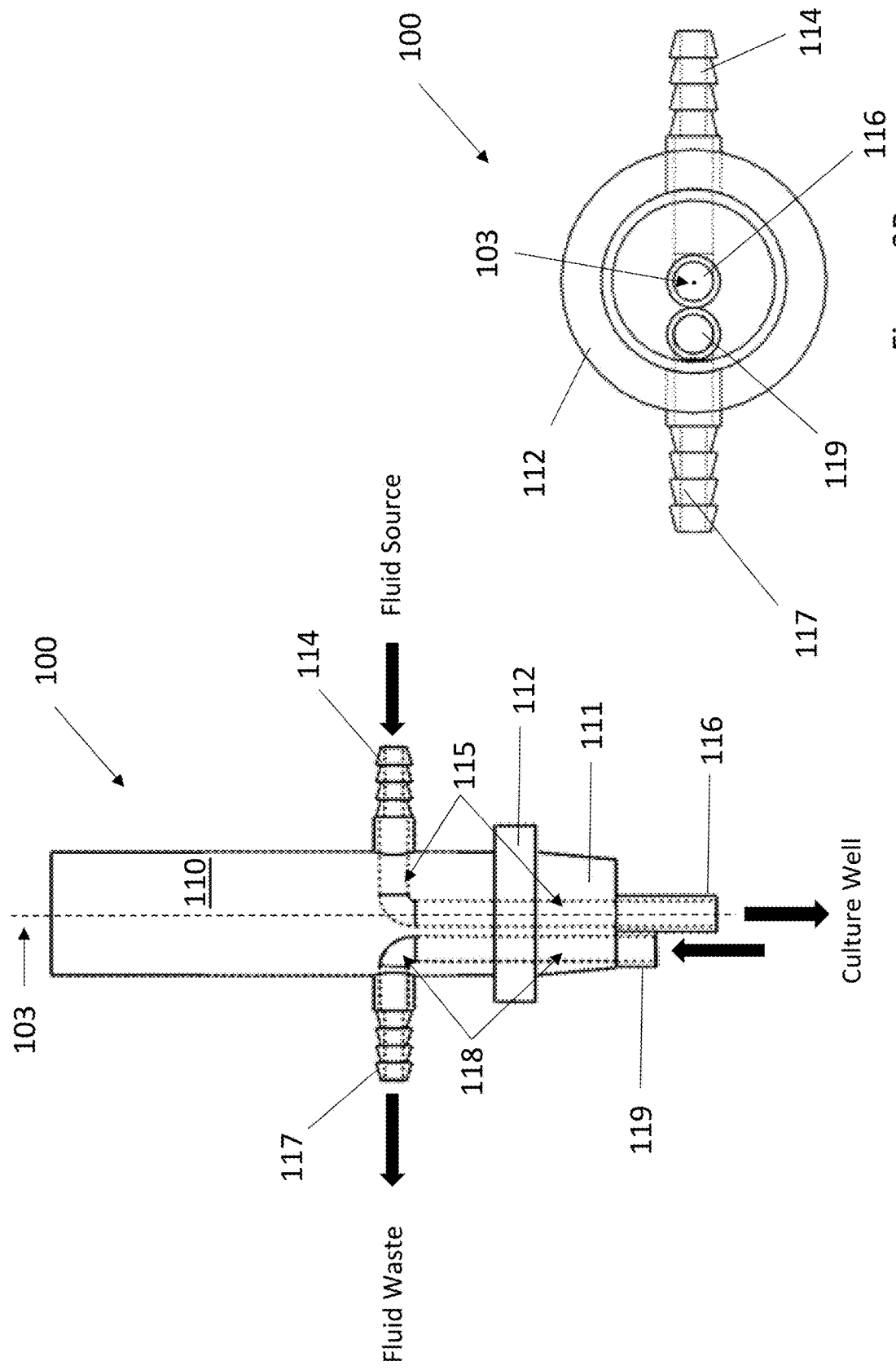
FIGS. 3A and 3B are front and bottom views of the FFD of FIG. 1.

As mentioned previously, FFD 100 further comprises a plurality of ports for managing fluid flow from a fluid source, into the desired culturing well, and out to a waste reservoir (or circulated through a common fluid reservoir). Referring now to FIGS. 3A and 3B, source fluid inflow port 114 is fluidly connected to well inlet port 116 by an internal conduit 115, thereby directing fluid to flow (block arrows) from a fluid source into the culturing well. Likewise, well outlet port 119 is fluidly connected to waste fluid outflow port 117 by an internal conduit 118, thereby directing fluid to flow from the well to a waste reservoir or common fluid reservoir. In some embodiments, FFD 100 may include more than one source fluid inflow port 114. In some embodiments, FFD 100 may include more than one waste fluid outflow port 117. In some embodiments, FFD 100 may include more than one well inlet port 116. In some embodiments, FFD 100 may include more than one well outlet port 119. In such embodiments where more than one port of the same type is present, FFD 100 may likewise include more than one conduit 115 and/or 118, or alternatively conduits 115 and/or 118 may have multiple junctions to join or separate the flow from various ports. In some embodiments, one or more valves (not shown) may be positioned in conduit 115 and/or 118, to regulate fluid flow by reducing or prohibiting fluid flow therethrough.

Source fluid inflow port 114 and waste fluid outflow port 117 may include barbs or ribbing on their exterior surface for engaging a soft tubing or other conduit, such that each port is fluidly connected to a fluid source and waste reservoir, respectively. Source fluid inflow port 114 and waste fluid outflow port 117 may otherwise include a fitting that is threaded, slip, compression, flare, flange, crimped, pressed, solvent welded, soldered, brazed, welded fitting, and the like. In one embodiment, inflow port 114 and outflow port 117 may include fitting configurations comprising straight, elbow, coupling, union, reducer, cross, cap and plug, nipple, valve, tee connections, and the like.

It should be appreciated that inflow and outflow ports 114 and 117, respectively, may be positioned at any desired location on elongate body 110 that is on, or proximal to, support flange 112. Further, inflow and outflow ports 114 and 117, respectively, may be positioned at any desired angle with respect to elongate body 110. For example, as shown in FIGS. 3A and 5A, inflow and outflow ports 114 and 117 may be positioned such that they extend outwardly from a central region of elongate body 110. In another embodiment, as shown in FIG. 4A, inflow and outflow ports 114 and 117, respectively, may be positioned such that they extend upward from the proximal end of elongate body 110.

Well inlet port 116 extends downward from the distal end of elongate body 110. In some embodiments, inlet port 116 extends vertically into the well, such that fluid flow exits inlet port 116 substantially perpendicular to a horizontal well floor. In other embodiments, inlet port 116 extends at an angle between 1 degree and 90 degrees with respect to the horizontal well floor. Similarly, well outlet port 119 extends downward from the distal end of elongate body 110. In some embodiments, outlet port 119 extends vertically into the well, and in other embodiments, outlet port 119 extends at an angle between 1 degree and 90 degrees with respect to the horizontal well floor. In some embodiments, well inlet port 116 extends into the culturing well further than well outlet port 119, as is shown in FIG. 3A. In other embodiments, such as is shown in FIGS. 4A and 5A, inlet and outlet ports 116 and 119 extend the same distance into the culturing well. In further embodiments, well outlet port 119 extends further into the culturing well than well inlet port 116. Accordingly, in some embodiments, when the inlet port 116 extends further than the outlet port 119, FFD 100 may be particularly suited for unidirectional flow through the further extending inlet port 116. Likewise, when inlet port 116 and outlet port 119 extend the same distance, FFD 100 may be particularly suited for multidirectional flow. It should be appreciated that while the various ports are described here as inlets and outlets, there is no limitation to the final directional flow through the device. In all embodiments, both well inlet port 116 and well outlet port 119 have a length that extends into the culturing well but do not make contact with the horizontal well floor, such that the inlet and outlet ports 116 and 119 do not touch any cellular or tissue growth on the horizontal well floor surface. In some embodiments, the distance between the distal tip of the well inlet port and the well floor is 2 mm to 4 mm. In some embodiments, the distance between the distal tip of the well outlet port 119 and the horizontal well floor is 2 mm to 10 mm.

Figure 9A:
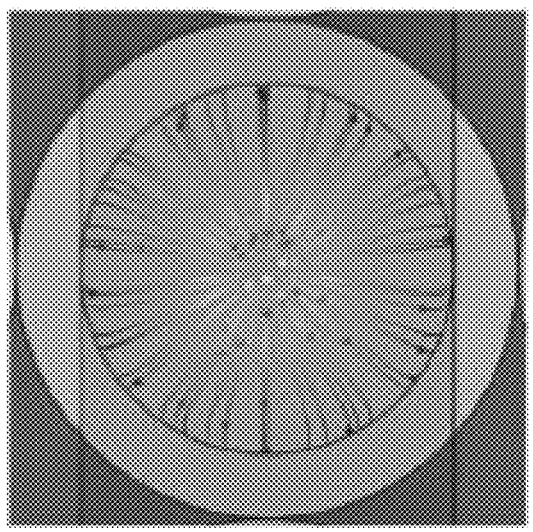
FIG. 9A through FIG. 9C depict vector lines indicating fluid flow trajectories.
Figure 9B:
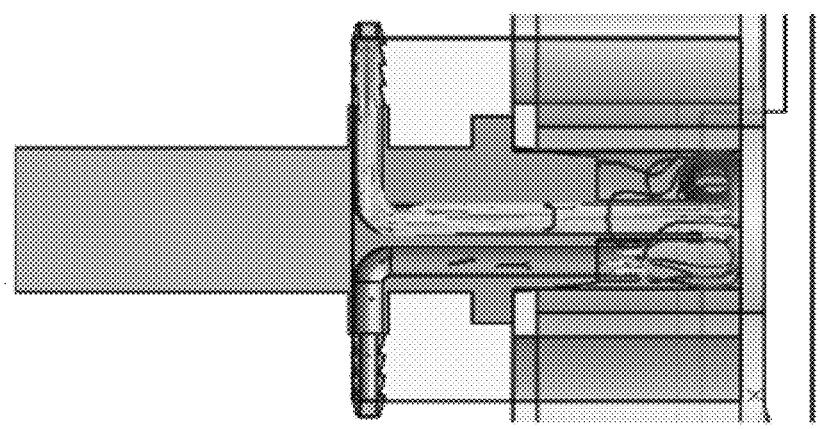

In some embodiments, well inlet port 116 may be centrally positioned, such that it is in line or concentric with a central axis 103 of elongate body 110, as is shown in FIGS. 3A and 3B. As such, as fluid flows into the culturing well, it circulates radially from well inlet port 116 and establishes laminar flow across the surface of the culturing well floor in which FFD 100 is placed, as is shown in FIGS. 9A and 9B. In such embodiments, well outlet port 119 may be positioned adjacent to inlet port 116 and offset from the central axis. In other embodiments, inlet and outlet ports 116 and 119 may be positioned adjacent to each other with a central axis 103 of elongate body 110 running between ports 116 and 119, as is shown in FIGS. 4A, 4B, 5A and 5B. In still other embodiments, well outlet port 119 may be centrally positioned, such that it is in line with a central axis 103 of elongate body 110, and well inlet port 116 may be positioned adjacent outlet port 119 and offset from the central axis 103. It should be appreciated that there is no limitation to the positioning of well inlet and outlet ports 116 and 119 relative to each other and relative to the central axis 103 of elongate body 110.

It should also be appreciated that the openings to each port, as well as the conduits between ports, can be of any desired shape and size, provided fluid can flow therethrough at the desired flow rate. For example, in some embodiments, the opening of source fluid inflow port 114 may have an inner diameter of 1 mm to 2 mm. In some embodiments, the opening of waste fluid outflow port 117 may have an inner diameter of 1 mm to 2 mm. In some embodiments, the opening of well inlet port 116 may have an inner diameter of 1 mm to 4 mm. In some embodiments, the opening of well outlet port 119 may have an inner diameter of 1 mm to 4 mm. In still other embodiment one or more of ports 114, 116, 117 and 119 may have a tapered or expanded end or opening, thereby altering the inner diameter and thus the flow rate of fluid therethrough. Likewise, conduits 115 and 118 may each have an inner diameter of 1 mm to 4 mm. Conduits 115 and/or 118 may have a constant inner diameter along its length, or it may have a variable inner diameter along its length.

FFD 100 may be constructed from any suitable material, such as stainless steel, aluminum, polymers, plastics, and the like. Such materials may optionally be biocompatible or non-bioreactive materials, and may be suitable for any use with any type of culturing media or other desirable liquid. FFD 100 may be constructed as a single unit or a multi-component assembled unit. FFD 100 or its component parts may be constructed via standard molding, casting, printing or any other techniques understood by those skilled in the art. In some embodiments, FFD 100 may be autoclavable, and in other embodiments it may be designed for single use and disposable.

Methods

The present invention also provides methods for shearing cultures of cells using the various embodiments of the FFD as described herein. In one embodiment, one or more FFDs is positioned in a well or wells of a multi-well plate having cells therein, such that the support flange secures the FFD to the well, and optionally seals the well. In various embodiments, the well is a well of a 384-well plate, a 96-well plate, a 24-well plate, a 12-well plate, a 6-well plate, a single well plate, and the like. A first tubing is connected to source fluid inflow port 114 and a fluid source, and a second tubing is connected to waste fluid outflow port 117 and waste reservoir. Alternatively, the first and second tubing can be connected to a common fluid reservoir to circulate the same fluid through the FFD. In some embodiments, the tubing is further connected to and in line with a pump, for example a peristaltic pump, a syringe pump, and the like. It should be appreciated that the choice of pump used will be based on the experimental parameters required; thus, the system can be tuned to the specific flow parameters required for a specific cell type or experimental variable, as desired. In some embodiments, the fluid is driven by gravity. That is, a fluid source reservoir connected to the inflow tubing is positioned at a height that is greater than a fluid collection reservoir connected to the outflow tubing. Accordingly, the difference in height of the two reservoirs drives flow through conduits of the FFD, applying shear stress to cells cultured in the well.

In some embodiments, the method comprises applying a shear stress that mimics a value for shear stress similar to what cells experience in situ. In some embodiments, a shear stress of 4 dynes/cm$^2$ is applied to the cells using the FFDs described herein. In some embodiments, a shear stress of 20 dynes/cm$^2$ is applied to the cells. In some embodiments, a shear stress of 1 dynes/cm$^2$ to 4 dynes/cm$^2$, 4 dynes/cm$^2$ to 10 dynes/cm$^2$, 10 dynes/cm$^2$ to 15 dynes/cm$^2$, 15 dynes/cm$^2$ to 20 dynes/cm$^2$, 20 dynes/cm$^2$ to 50 dynes/cm$^2$, or more than 50 dynes/cm$^2$ is applied to the cells. In some embodiments, the shear stress is adjusted by adjusting the fluid flow rate entering the FFD. In some embodiments, the shear stress is adjusted by adjusting the fluid flow rate at one or more points within a conduit and/or a port of the FFD. In some embodiments, the shear stress is adjusted by adjusting the viscosity of the fluid. It should be appreciated that the shear stress may additionally be adjusted by any other means understood by those skilled in the art.

In some embodiments, the method includes applying physiological pressure to cultured cells. In some embodiments, the applied dynamic pressure is about 1 dynes/cm$^2$. In some embodiments, the dynamic pressure is about 750 dynes/cm$^2$. In some embodiments, the dynamic pressure is about 10 dynes/cm$^2$, about 25 dynes/cm$^2$, about 50 dynes/cm$^2$, about 75 dynes/cm$^2$, about 100 dynes/cm$^2$, about 250 dynes/cm$^2$, about 500 dynes/cm$^2$, and about 750 dynes/cm$^2$. In some embodiments, the inlet dynamic pressure is about 500 dynes/cm$^2$.

In some embodiments, for example when the FFD well inlet port is centrally positioned concentric with the central axis of the FFD, and extends a greater distance into the culturing well than outlet port, a uniform flow field is established directed radially from the well inlet port, across the surface of the well floor, to the well outlet port, such that laminar flow is developed so that cells are sheared with laminar or uniform shear stress. In some embodiments, for example when the FFD well inlet and outlet ports are adjacent, the central axis running between the inlet and outlet ports, and inlet and outlet ports extend the same distance into the culturing well, an oscillatory flow field is established, and turbulent, nonlaminar or oscillatory flow is developed so that cells are sheared with nonlaminar shear stress.

As shown in FIG. 6, two or more FFDs can be used concurrently in a multiplexed array configuration. In some embodiments, the two or more FFDs can use the same or separate fluid source reservoir and/or pumps. In some embodiments, the two or more FFDs are used for high-throughput molecular and biochemical analysis of cells, such as ELISA, Western blotting, mass spectrometry, and other assays understood by those skilled in the art. In some embodiments, the one or more FFDs are used for imaging studies, such as imaging with a microscope or other tool or technique known to one skilled in the art. In some embodiments, the one or more FFDs are used for molecular and biochemical analysis of cells and imaging studies simultaneously or in the same or similar experiments thereby reducing experimental variability.

Kits

In one aspect, the present invention also includes a kit comprising instrumentation to apply fluid flow to cells plated in a culture plate. In certain embodiments, the kit is a sterile packaged kit. In certain embodiments, the one or more instruments of the fluid flow kit are sterile and contained in one or more individual sterile packages within the kit. The sterile fluid flow kit contemplated herein is thus immediately ready for shear stress application upon removal of the instruments from their respective packages without the need for pre-operation cleaning, sterilizing, or other processing. In certain aspects, the one or more instruments of the fluid flow kit are single-use instruments. For example, in one embodiment, the one or more instruments of the fluid flow kit are sterile and disposable. In another embodiment, the one or more instruments of the fluid flow kit are repackaged after use, where, in certain embodiments, the one or more instruments may be reprocessed for future use. In one embodiment, the instruments may be provided in one or more blister packaging. Each blister may comprise a plastic container (e.g., PETG) component and a lid (e.g., Tyvek®) component.

In certain embodiments, the fluid flow kit comprises at least one FFD as described herein. In certain embodiments, the fluid flow kit may optionally include other instruments, such as and without limitation, one or more fittings, tubing, pumps, and/or reservoirs. For example, in one embodiment, the fluid flow kit comprises one or more fittings, which may be barbed fittings, threaded, slip, compression, flare, flange, crimped, and/or pressed fittings or the like, or a combination thereof. In one embodiment, the fluid kit comprises one or more lengths of tubing, including any size or geometry of tubing which may be necessary for the desired application. In one embodiment, the tubing is composed of Tygon®, nylon, polyethylene, or other suitable material known to one skilled in the art. In one embodiment, the tubing comprises one or more stops for integration into holders of a peristaltic pump. In one embodiment, the fluid flow kit comprises one or more pumps. In one embodiment, the one or more pumps are peristaltic pumps, syringe pumps, or the like, as known to one skilled in the art. In one embodiment, the fluid flow kit may include one or more culturing wells or multi-well plates. In one embodiment, the fluid flow kit may include culturing media or culturing media components for admixing. In one embodiment, the fluid flow kit may include a biological material, such as a cell or tissue.

In certain embodiments, the fluid flow kit is custom-configured with regard to size and geometry appropriate to the well being used. In one embodiment, the kit is configured for a specific size of cylindrical body or flange. In an alternative embodiment, the kit comprises instrumentation that may be necessary for various sizes of wells.

In certain embodiments, the kit comprises instructional material. Instructional material may include a publication, a recording, a diagram, or any other medium of expression which can be used to communicate the usefulness of any of the FFDs or fluid flow kit components described herein. The instructional material may also include description of one or more steps to perform any of the methods described herein. The instructional material of the kit may, for example, be affixed to a package which contains one or more instruments which may be necessary for the desired procedure. Alternatively, the instructional material may be shipped separately from the package, or may be available electronically, such as accessible from the Internet, or any downloadable electronic document file format.

Still further, the present invention includes a method of providing a sterile fluid flow kit as described herein. In certain embodiments, the method comprises receiving a request for one or more instruments for use in shearing cells or the like. In certain embodiments, the method comprises a customized request for particular instrumentation. In certain embodiments, the method comprises a request for a standardized kit which would contain the one or more instruments. In certain instances, the method comprises gathering the one or more instruments which were requested. In one embodiment, the method comprises processing the one or more instruments. For example, in one embodiment, the one or more instruments are sterilized. Sterilization of the one or more instruments may be conducted by any suitable method known in the art. In one embodiment, the method comprises packaging the one or more instruments. For example, the one or more instruments may be packaged in one or more sterile packages to form a sterile kit.

It should be appreciated that the devices and the fluid flow kits described herein may be used for a variety of fluid flow or shear stress procedures including but not limited to shearing cells, tissue, biological samples, non-biological samples, and the like. The procedures may be performed on any cell in the human or vertebrate body, including, but not limited to, osteocytes, osteoblasts, osteoclasts, endothelial cells, epithelial cells, smooth muscle cells, mesenchymal cells, progenitor cells, and the like. It should be understood that the present disclosure is not limited to a specific cell, tissue, or fluid flow application.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the devices of the present invention and practice the claimed methods. The following working examples therefore and are not to be construed as limiting in any way the remainder of the disclosure.

Example 1. Computational Fluid Dynamics Model

Computational Modeling

Figure 7C:
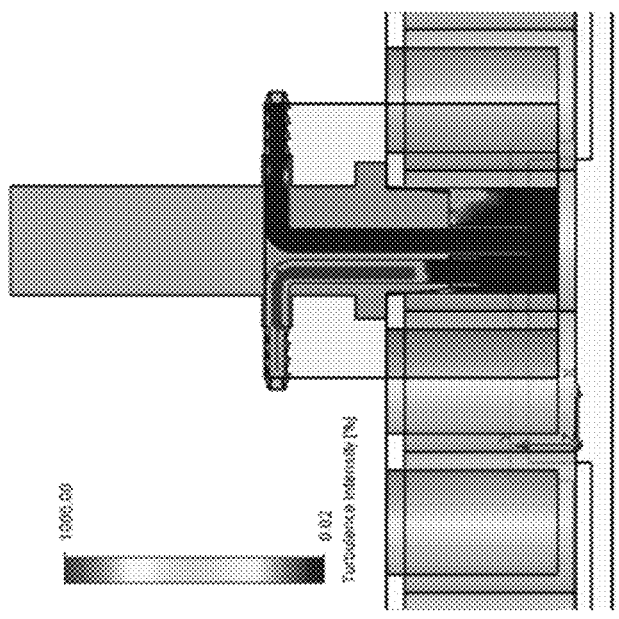
FIG. 7A through FIG. 7C depict the results of a computational fluid dynamics simulation.
Figure 7B:
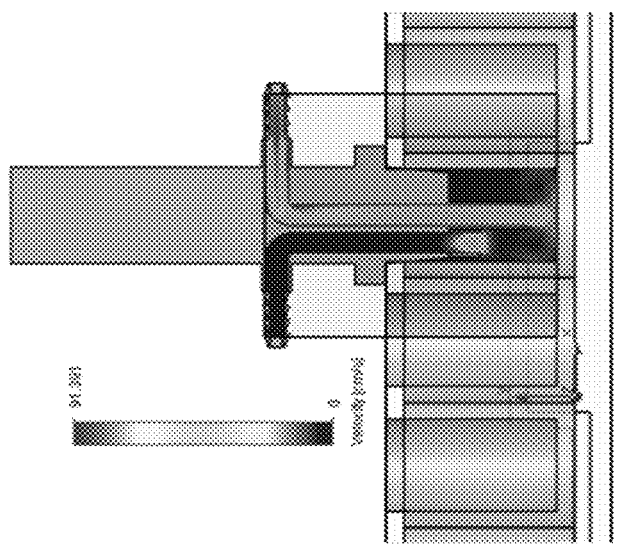
Figure 7A:
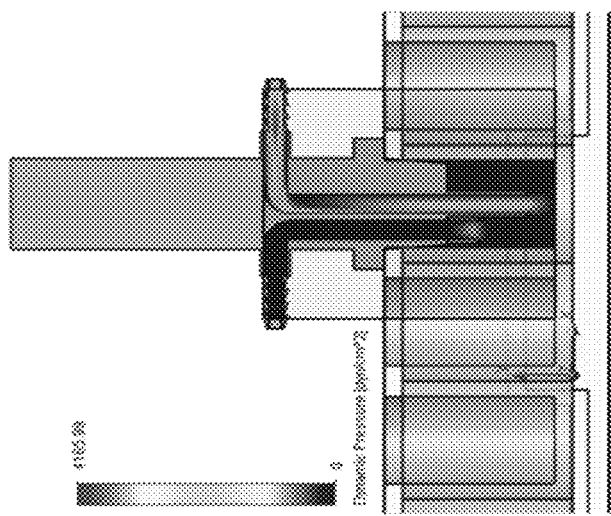

SolidWorks 2015 Flow Simulation software was used to perform computation fluid dynamics on the device and simulate the flow environment inside the well during flow (FIGS. 7A-7C). The device was drawn to scale and capped at the beginning of the inlet and the end of the outlet to form a closed geometry. Two boundary conditions were set for the flow simulation, inlet pressure and outlet flow volume. In order to determine the pressure, the known inlet diameter and flow rate was used. First the flow velocity (cm/sec) was calculated using the known flow rate set by the pump and area of the inlet (calculated from the known diameter) using Equation 1:

$$v = \frac{Q}{A} \quad (1)$$

Where v=velocity, Q=flow rate, and A=area of the inlet. Using the calculated velocity the pressure was calculated in Pascals using the Navier-Stokes equation, simplified to the Bernoulli's equation, Equation 2.

$$\frac{1}{2}\rho V^2 + p + \rho gz \quad (2)$$

Where ρ=density, V=velocity, p=pressure, g=gravity, and z=height. In order for Bernoulli's principle to hold true for the system, the following assumptions were made: (1) Flow buffer is a Newtonian fluid, (2) the flow is incompressible, and (3) there is no friction inside the flow.

For all simulations, the flow buffer was assumed to be similar to water and thus, density=1000 kg/ml. The computational solver calculated flow velocity (FIG. 8), flow trajectories (FIGS. 9A-9C), average shear stress at the bottom surface of the well (FIG. 7C), turbulence intensity (FIG. 7C), and dynamic pressure (FIG. 7A.) inside the well. It is important to note, the boundary conditions used to run these simulations were determined from experimental data and what elicited the expected biological outcome based on published reports.

Figure 8:
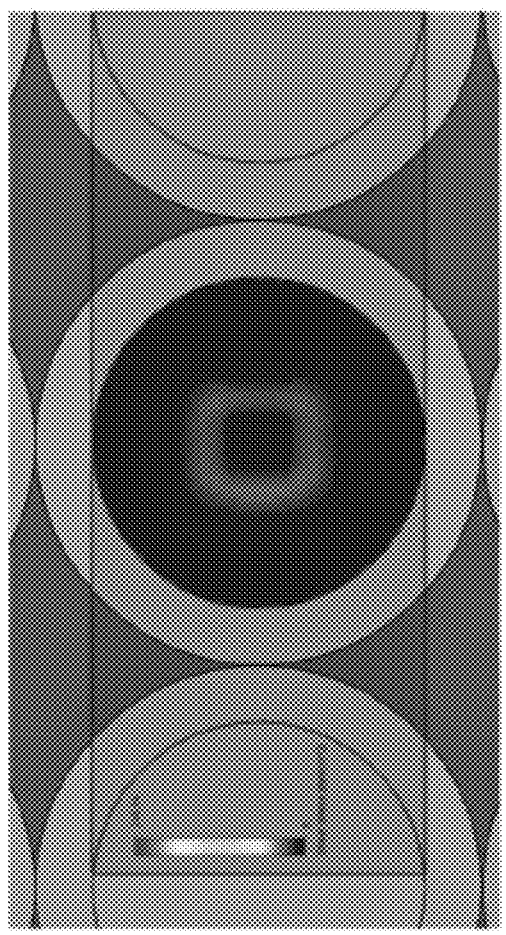
FIG. 8 illustrates simulated shear stress at the bottom surface of the well. Computational trace of the average shear stress at the bottom surface of the well over time. Data were determined using Solid Works 2015 Flow Simulation software.
Figure 8:
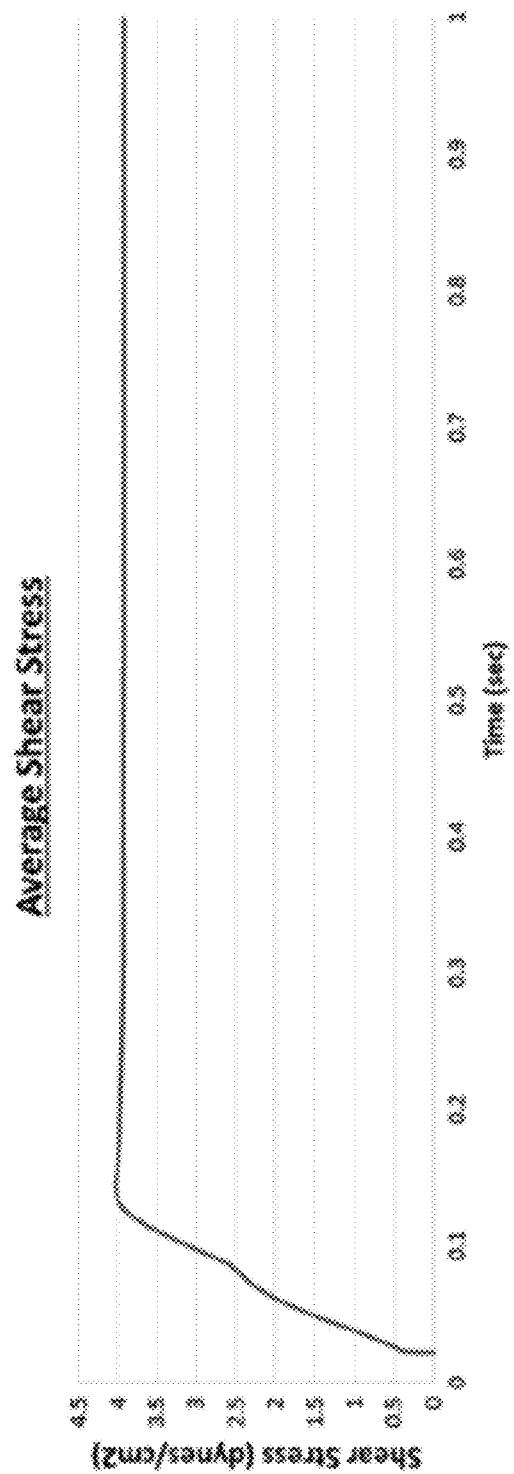
Figure 9C:
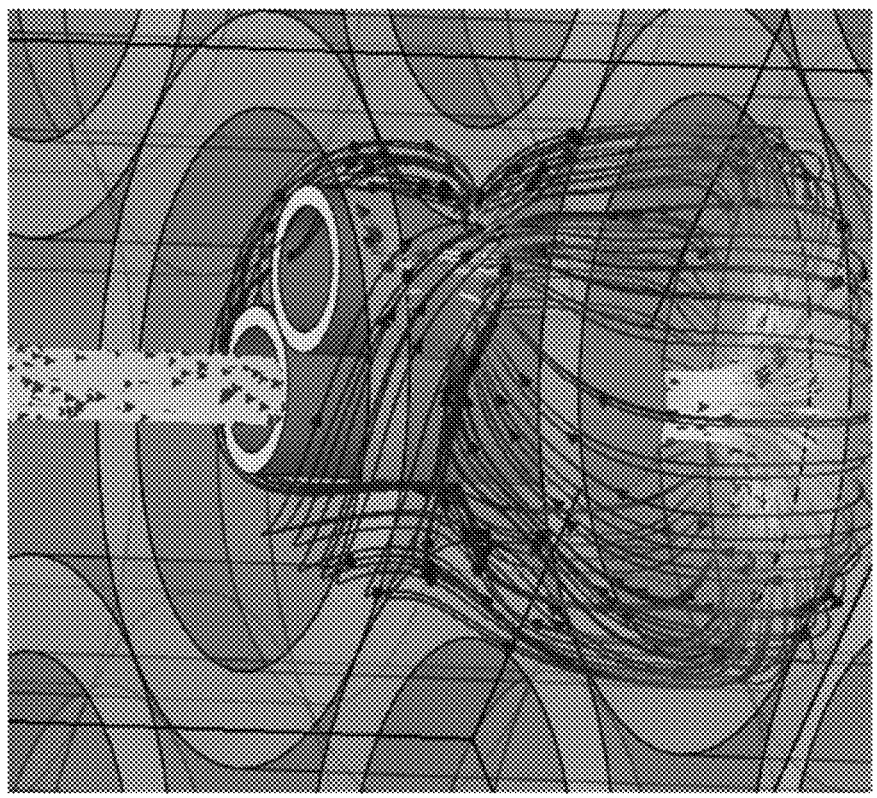

The results of the simulation indicate that the bottom surface of the well where the cell monolayer resides is subjected to a nearly uniform average 4 dynes/cm² of shear stress (FIG. 8). Further, the velocity trajectories indicate that the flow across the bottom surface of the well is almost perfectly uniform such that the entire well of cells is subjected to the same forces. Interestingly, the turbulence intensity within the system is extremely low, 0.65%. These findings indicate that the flow system approximately mimics in vivo physiologic fluid shear stresses.

Device Validation

Figure 10:
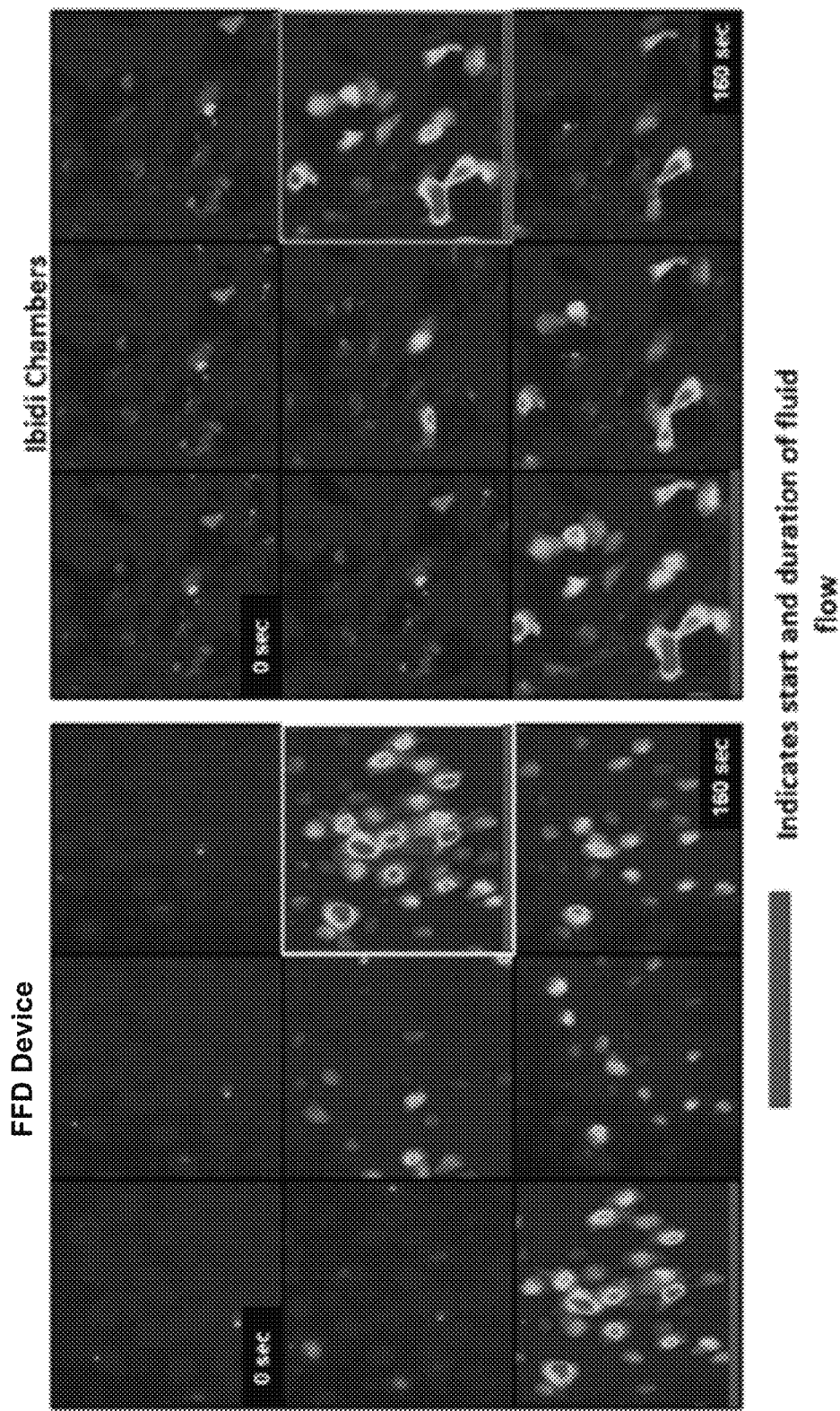
FIG. 10 through FIG. 12 depict the results of real-time Ca$^{2+}$ imaging of UMR106 cells during application of fluid flow.
Figure 11:
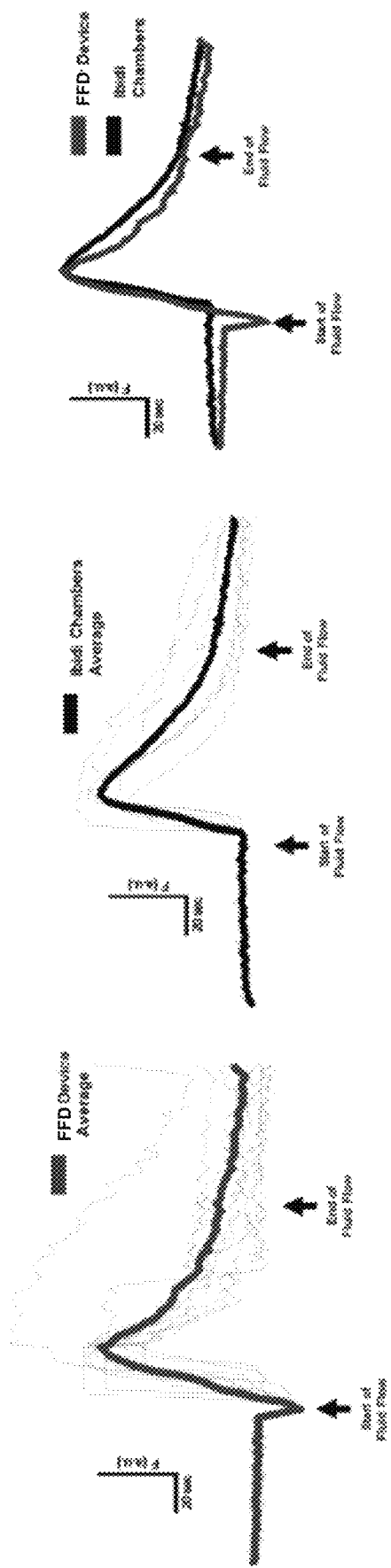
Figure 12:
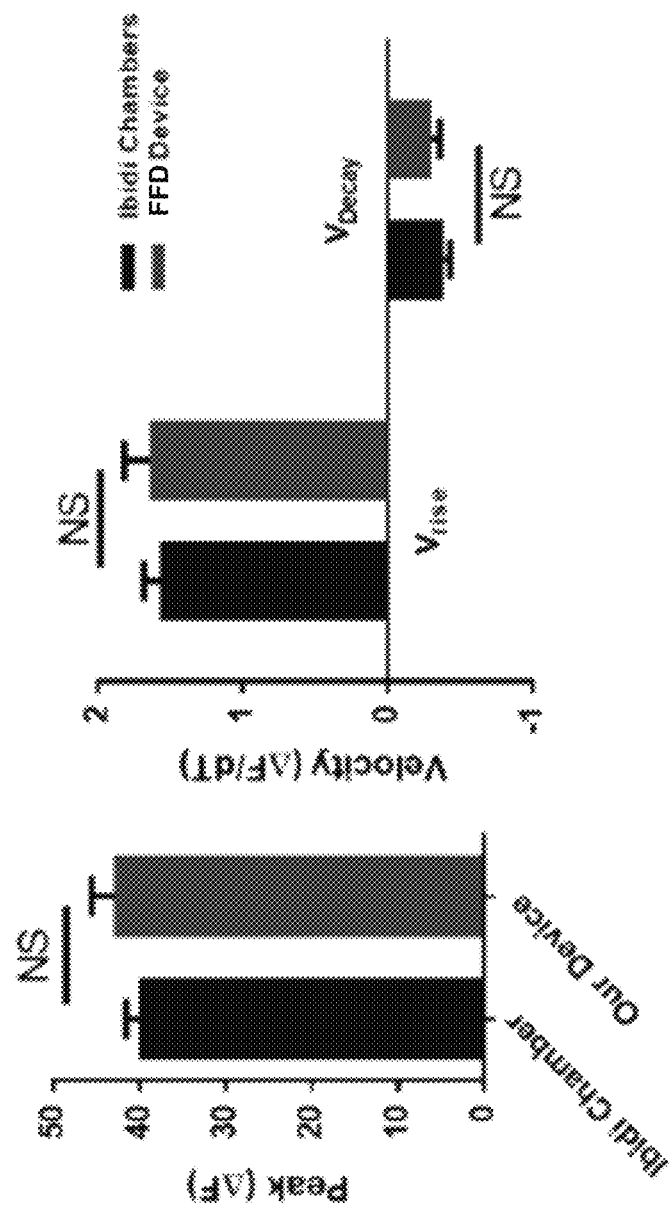

In order to validate the design of the fluid flow device, the biological response elicited by the FFD device was compared to other commercially available models. It is established that UMR106 osteoblast-like cells are mechanoresponsive and that fluid flow induces a rapid calcium influx across the plasma membrane. Therefore, this cell line was used to compare the device of the present invention to the commercially available and widely accepted Ibidi chamber slides for real-time live cell imaging. The Ibidi slides are known to produce laminar flow and biologically relevant shear stress on cells cultured within the chambers. UMRI06 cells were seeded in an Ibidi μ-slide I and loaded the cells with a calcium indicator dye, Fluo-4. Similarly, UMRI06 cells were seeded into a 96-well plate with a special optics bottom. The same Gilson Minipuls 3 peristaltic pump was used for both conditions. The pump flow rate was adjusted to achieve the same fluid shear stress as previously reported for the Ibidi chambers. When the response of UMRI06 cells were compared in both conditions, an almost identical response was shown (FIG. 10). Not only do both conditions show similar kinetics of the response (FIG. 11), but they also both show a similar peak change in fluorescence (FIG. 12).

Figure 13:
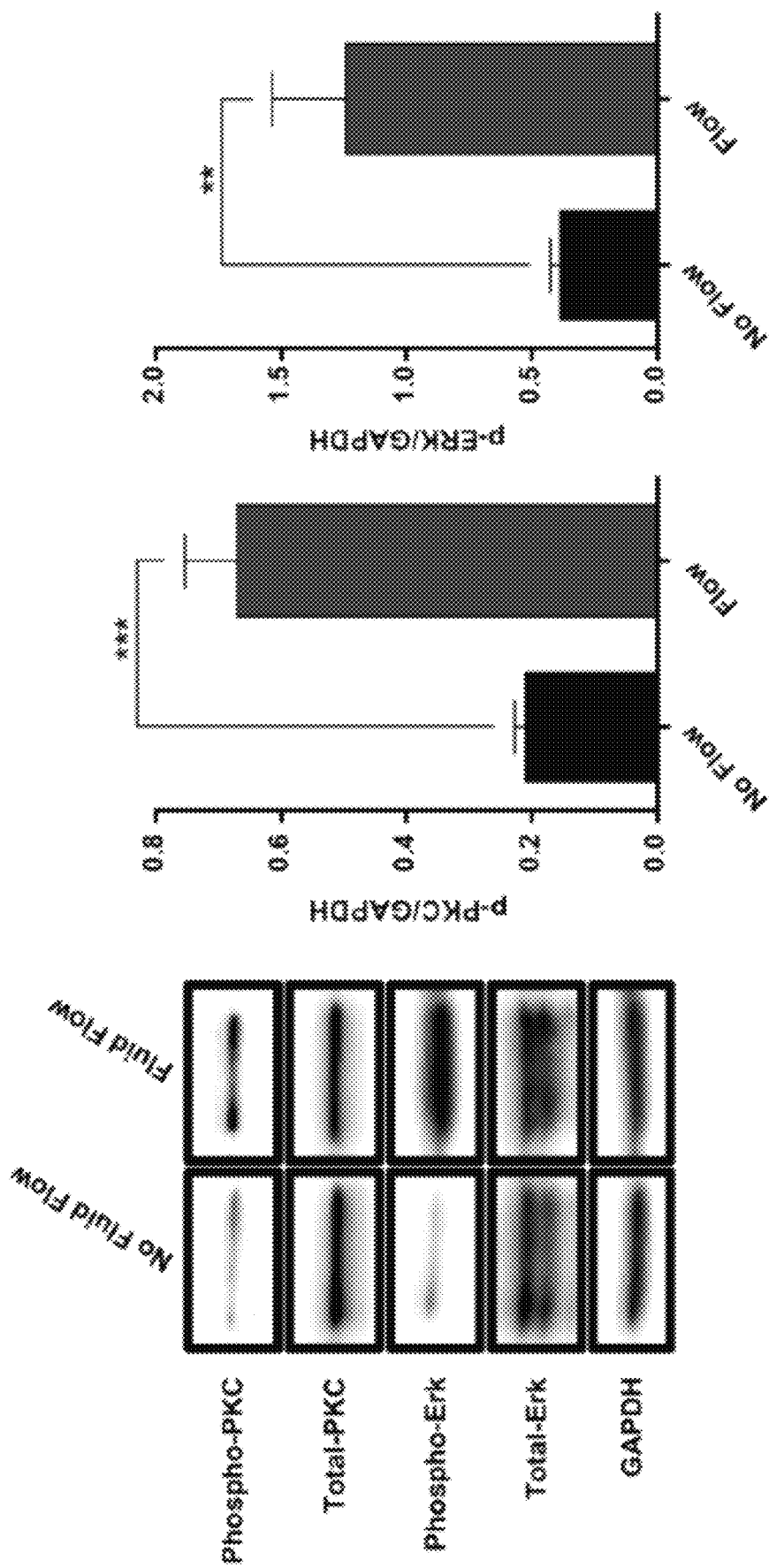
FIG. 13 illustrates western blot analysis of UMR106 cells exposed to fluid flow in the FFD. Fluid flow induced rapid activation of PKC signaling and ERK signaling as indicated by an increase in phosphorylated PKC and phosphorylated ERK. Data are from the same gel and exposure. Image J quantification of western blot relative to GAPDH. Double asterisks () indicate statistical significance at p<0.01. Triple asterisks (*) indicate statistical significance at p<0.001.

To further validate the FFD design, the activation of fluid flow induced signaling was evaluated. It has been reported previously that fluid flow shear stress causes activation of ERK signaling in UMRI06 cells. Therefore, cells were seeded in a 96-well tissue culture treated plate and subjected the cells to 4 dynes/cm² of fluid shear stress. After flow, the cells were immediately lysed using a modified RIPA buffer. Whole cell lysates were then separated by SDS-PAGE for Western blot analysis. It was observed that with the system of the present invention, fluid flow induces rapid activation of ERK signaling as indicated by an increase is phosphorylated-ERK (FIG. 13).

These data suggest that the FFD design generates physiologic fluid flow shear stress conditions comparable to the accepted commercially available methods.

In conclusion, the fluid flow device of the present invention overcomes a variety of drawbacks that are associated with currently available models. The FFD is highly versatile in its functionality and costs substantially less. Also, the device delivers physiologically relevant fluid flow conditions to cells in monolayer culture. Furthermore, the device elicits similar biological responses in osteoblast-like cells as is commonly accepted in the field. Overall, the FFD provides an improved method for studying the response of not only bone cells but any mechano-responsive cell type in vitro and will help advance the study of mechanotransduction.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:
1. A fluid flow device, comprising:
an elongate tubular body having an upper proximal end, a lower distal end, and a length therebetween, the distal end of the elongate tubular body configured for insertion into a well of a multiwell cell culture plate;
at least one first source port positioned on the distal end;
at least one first waste port positioned on the distal end;
at least one second source port positioned on the elongate tubular body above the at least one first source port;
at least one second waste port positioned on the elongate tubular body above the at least one second waste port;
at least one source conduit positioned within the body connecting a single first source port to a single second source port; and at least one waste conduit positioned within the body connecting a single first waste port to a single second waste port.

2. The fluid flow device of claim 1, wherein one of the at least one first source port is aligned in parallel with a central longitudinal axis of the elongate tubular body and is positioned centrally on the distal end.

3. The fluid flow device of claim 1, wherein the at least one first source port and the at least one first waste port each extends from the distal end of the elongate tubular body for a length, such that the length of the at least one first source port extends further than the length of the at least one first waste port.

4. The fluid flow device of claim 1, wherein the at least one first source port and the at least one first waste port extend for an equal length from the distal end of the elongate tubular body.

5. The fluid flow device of claim 1, wherein the distal end of the elongate tubular body is tapered.

6. The fluid flow device of claim 1, wherein the at least one second source port and the at least one second waste port each extend outwardly for a length in a lateral direction away from the elongate tubular body.

7. The fluid flow device of claim 1, wherein the at least one second source port and the at least one second waste port each extend upward from the proximal end of the elongate tubular body.

8. The fluid flow device of claim 1, further comprising a flange positioned adjacent to the distal end of the elongate tubular body.

9. A high-throughput fluid flow assembly, comprising:
a plurality of fluid flow devices of claim 1, wherein the fluid flow devices are physically connected such that a central longitudinal axis of each elongate tubular body of the fluid flow devices are in parallel alignment.

10. The assembly of claim 9, wherein the at least one second source port of each respective fluid flow device are fluidly connected to a shared fluid source.

11. The assembly of claim 9, wherein the at least one second waste port of each respective fluid flow device is fluidly connected to a shared fluid reservoir.

12. A fluid flow kit, comprising at least one fluid flow device of claim 1 and one or more component selected from the group consisting of: a fitting, a tubing, a pump, a reservoir, and a multi-well plate.

13. A method of applying fluid flow to biological cells in a culturing well, comprising:
positioning the device of claim 1 in a culturing well of the multiwell cell culture plate, such that the at least one first source port and at least one first waste port are positioned within the culturing well;
connecting a first tubing to the at least one second source port;
connecting a second tubing to the at least one second waste port; and
flowing a fluid through the first tubing;
wherein the fluid applies a shear stress to cells in the culturing well.

14. The method of claim 13, wherein a pump in line with the first tubing is used to flow the fluid.

15. The method of claim 14, wherein a flow rate of the fluid is adjustable using the pump.

16. The method of claim 15, wherein the flow rate is adjusted such that the shear stress is about 4 dynes/cm$^2$.

* * * * *